United States Patent
Gharpure et al.

(10) Patent No.: US 10,428,033 B2
(45) Date of Patent: Oct. 1, 2019

(54) PROCESS FOR THE PREPARATION OF VORTIOXETINE AND SALTS THEREOF

(71) Applicant: PIRAMAL ENTERPRISES LIMITED, Mumbai (IN)

(72) Inventors: Milind Gharpure, Mumbai (IN); Sanjay Kumar Sharma, Mumbai (IN); Nainesh Kansagara, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

(21) Appl. No.: 15/896,193

(22) Filed: Feb. 14, 2018

(65) Prior Publication Data

US 2018/0230116 A1 Aug. 16, 2018

(30) Foreign Application Priority Data

Feb. 15, 2017 (IN) .............................. 201721005320

(51) Int. Cl.
   *C07D 295/096* (2006.01)
   *C07B 43/04* (2006.01)
   *C07C 211/46* (2006.01)

(52) U.S. Cl.
   CPC .......... *C07D 295/096* (2013.01); *C07B 43/04* (2013.01); *C07C 211/46* (2013.01)

(58) Field of Classification Search
   CPC ................................................. C07D 295/096
   See application file for complete search history.

(56) References Cited

U.S. PATENT DOCUMENTS

| 7,144,884 B2 | 12/2006 | Ruhland et al. |
| 9,095,588 B2 | 8/2015 | Faldt et al. |
| 9,493,409 B2 | 11/2016 | Zupancic |
| 2016/0060215 A1 | 3/2016 | Zupancic |

FOREIGN PATENT DOCUMENTS

| CN | 103788019 A | 5/2014 |
| CN | 103788020 A | 5/2014 |
| CN | 103936694 A | 7/2014 |
| CN | 104098530 A | 10/2014 |
| CN | 104109135 A | 10/2014 |
| WO | 2014/161976 A1 | 10/2014 |
| WO | 2015/114395 A1 | 1/2015 |
| WO | 2016/004908 A1 | 1/2016 |

OTHER PUBLICATIONS

CN 103788019 A _ English Abstract.
CN 103788020 A_ English Abstract.
CN 103936694 A_ English Abstract.
CN 104098530 A_ English Abstract.
CN 104109135 A_ English Abstract.

*Primary Examiner* — Bruck Kifle
(74) *Attorney, Agent, or Firm* — Ladas & Parry LLP

(57) ABSTRACT

The present invention provides an improved process for preparation of 1-[2-(2,4-dimethyl-phenylsulfanyl)-phenyl]-piperazine; commonly known as vortioxetine (referred to as the compound (I)) and pharmaceutically acceptable salts thereof; wherein the process comprises reaction of 2-((2,4-dimethylphenyl)thio)aniline (II) with bis(2-alkyl)amine (IIIa) or its salt in the presence of a cyclic amide solvent.

9 Claims, No Drawings

PROCESS FOR THE PREPARATION OF VORTIOXETINE AND SALTS THEREOF

FIELD OF THE INVENTION

The present invention relates to an improved process for the preparation of 1-[2-(2,4-dimethyl-phenylsulfanyl)-phenyl]-piperazine; commonly known as vortioxetine (referred to as the compound (I)) and pharmaceutically acceptable salts thereof.

BACKGROUND OF THE INVENTION

The following discussion of the prior art is intended to present the invention in an appropriate technical context, and allows its significance to be properly appreciated. Unless clearly indicated to the contrary, reference to any prior art in this specification should not be construed as an expressed or implied admission that such art is widely known or forms part of common general knowledge in the field.

Vortioxetine (the Compound (I)), is a typical antidepressant indicated for the treatment of major depressive disorder and marketed under the brand name as TRINTELLIX. The marketed compound is in the form of its hydrobromide salt which is chemically known as 1-[2-(2,4-dimethyl-phenylsulfanyl)-phenyl]-piperazine, hydrobromide, and is structurally represented as follows;

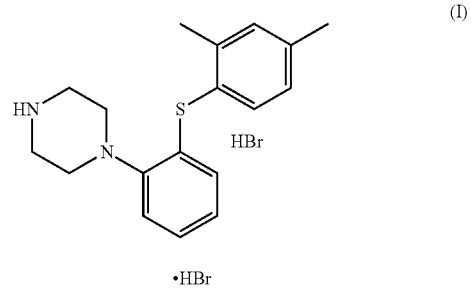 [SMILES: Cc1ccc(Sc2ccccc2N2CCNCC2)c(C)c1 ; Br ; Br]

Vortioxetine being an important antidepressant agent; a number of processes for its preparation as well as for its intermediates are known in the art.

U.S. Pat. No. 7,144,884 refers to the phenylsulfanyl-piperazine compounds, wherein generically as well as with analogous compounds, it describes a process for the synthesis of vortioxetine comprising the reaction of amine compound with an alkylating agent as depicted below; however the patent does not provide any specific reaction conditions:

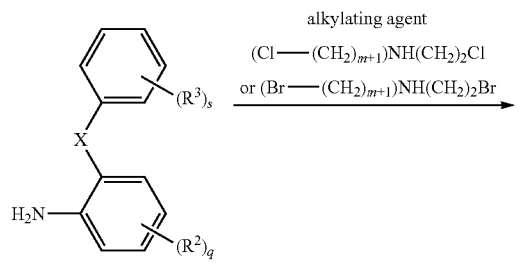

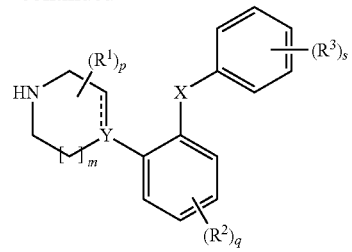

U.S. Pat. No. 9,493,409 describes a process for the preparation of vortioxetine consisting of reacting 2-((2,4-dimethylphenyl)thio)aniline with bis(2-chloroethyl)amine hydrochloride in the presence of diethylene glycol methyl ether at 130° C. for 3 days to provide the product as vortioxetine hydrochloride as white powder with 53% yield.

Published PCT application WO 2016/004908 A1 describes a process for the preparation of 1-(2-(2,4-dimethylphenylsulphanyl)phenyl)piperazine comprising reaction of 2-(2,4-dimethylphenyl sulphanyl) benzeneamine with a suitable precursor of formation of piperazine ring in an aromatic solvent selected from the group consisting of chlorobenzene, xylene, toluene, α,α,α-trifluorotoluene and their mixtures, to provide product with overall 50% yield.

Chinese patent application CN 103788019 describes a process for the preparation of 1-(2-(2,4-dimethylphenylsulphanyl)phenyl)piperazine comprising cyclization reaction of 2-(2,4-dimethylphenylsulphanyl) benzeneamine with a suitable precursor as bis (2-haloethyl) amine; wherein the said cyclization reaction is carried out in the presence of an acid binding agent such as triethylamine, pyridine, N-methylmorpholine, diisopropylethylamine or 4-dimethylaminopyridine.

In addition to the afore discussed patent documents, there are a number of patent documents that describe a process for the preparation of vortioxetine, its intermediates and salts thereof. For instance, published PCT application WO2015114395 and WO2014161976A1; published US patent application 2016/0060215; Chinese patent applications CN 103788020, CN 103936694, CN 104109135, CN104098530; U.S. Pat. No. 9,095,588 B2 describes a process for the preparation of vortioxetine and its salts.

It is evident from the discussion of the processes for the preparation of vortioxetine and its salts, described in the afore cited patent documents that the reported processes provide a product with low yield and purity, which requires repeated purification or multiple crystallization steps. Also, the prior art process also refers the use of various reagents and coupling agents such as acid binding agent, metal catalyst or a phosphine ligand; which renders the process costlier and hence are not industrially feasible. In view of these drawbacks, there is a need to develop an industrially viable commercial process for the preparation of vortioxetine; which is a simple, efficient and cost-effective process and provides the desired compounds in improved yield and purity.

Inventors of the present invention have developed an improved process that addresses the problems associated with the processes reported in the prior art. The process of the present invention does not involve use of any toxic and/or costly solvents, also does not involve use of costlier coupling agents and reagents. Moreover, the process does not require repetitive purification steps. Accordingly, the present invention provides a process for the preparation of vortioxetine, which is simple, efficient, cost effective, environmentally friendly and commercially scalable for large scale operations.

SUMMARY OF THE INVENTION

In one aspect, the present invention relates to an improved process for the preparation of vortioxetine (the compound (I)) or its salt, comprising reacting the compound (II) (as described herein) with the compound (IIIa) (as described herein) or its salt in a cyclic amide solvent.

In one aspect, the present invention relates to an improved process for the preparation of vortioxetine (the compound (I)) or its salt, comprising reacting the compound (II) (as described herein) with the compound (III) (as described herein) or its salt in a cyclic amide solvent.

In one aspect, the present invention relates to an improved process for the preparation of vortioxetine (the compound (I)) or its salt, comprising reacting the compound (II) (as described herein) with the compound (IIIa) (as described herein) or its salt in a cyclic amide solvent at temperature ranging between 80-180° C.; and optionally transforming vortioxetine salt into its another acid salt.

According to another aspect of the present invention, there is provided an improved process for the preparation of vortioxetine (the compound (I)) or its salt, wherein the said compound (I) is obtained in a yield of about 70% and purity of more than about 99% (HPLC).

In another aspect, there is provided Vortioxetine (I) hydrobromide having particle size distribution range of d (10) of about less than 12 μm, d (50) of about less than 40 μm or d (90) of about less than 180 μm; or any combination thereof.

In another aspect, there is provided Vortioxetine (I) hydrobromide having specific surface area value from 0.05 to 2 m$^2$/g.

DETAILED DESCRIPTION OF THE INVENTION

Accordingly, the present invention relates to an improved process for the preparation of vortioxetine (the compound (I)) or its salt represented by the following formula,

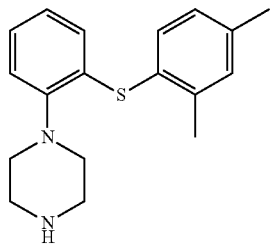
(I)

comprising; reacting 2-((2,4-dimethylphenyl)thio)aniline (the compound (II)) represented by the following formula;

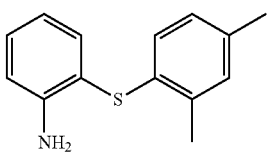
(II)

with bis(2-alkyl)amine (the compound (IIIa)) or its salt represented by the following formula;

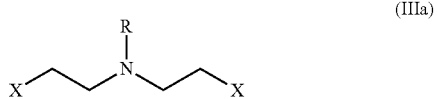
(IIIa)

wherein, X is a leaving group and R is H or a protecting group
in a cyclic amide solvent, either providing compound (I) directly if R is H; or providing compound (Ia) if R is a protecting group,

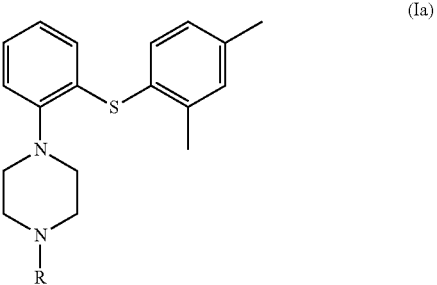
(Ia)

which on deprotection provides compound (I).

Accordingly, there is provided an improved process for the preparation of vortioxetine (the compound (I)) or its salt represented by the following formula,

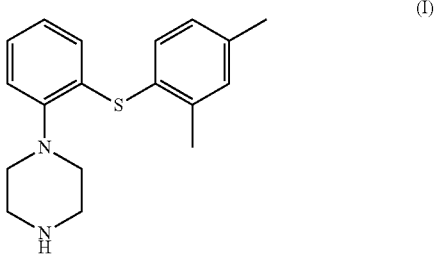 [SMILES: Cc1ccc(Sc2ccccc2N2CCNCC2)c(C)c1]
(I)

comprising; reacting 2-((2,4-dimethylphenyl)thio)aniline (the compound (II)) represented by the following formula;

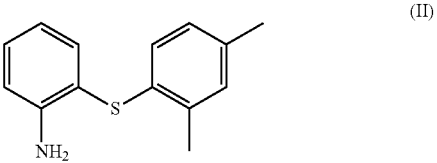 [SMILES: Cc1ccc(Sc2ccccc2N)c(C)c1]
(II)

with bis(2-alkyl)amine (the compound (IIIa)) or its salt represented by the following formula;

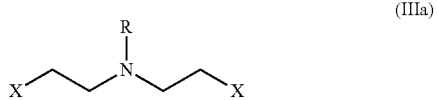
(IIIa)

wherein, X is a leaving group and R is H or a protecting group in a cyclic amide solvent at temperature ranging between 80-180° C.; either providing compound (I) directly if R is H; or providing compound (Ia) if R is a protecting group,

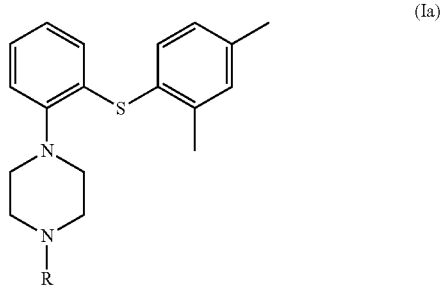

(Ia)

which on deprotection provides compound (I);

and optionally transforming vortioxetine or its salt into its another acid salt.

In the context of the present invention, the term "optionally" when used in reference to any element; including a process step e.g. conversion of a compound; it is intended to mean that the subject element is subsequently converted, or alternatively, is not converted to a further compound. Both alternatives are intended to be within the scope of the present invention.

In an embodiment, the cyclic amide solvent is selected from the group consisting of N-methyl-2-pyrrolidone, caprolactam, 2-piperidinone, azetidin-2-one, N-methyl caprolactame, 1-methylpiperidin-2-one and 1-methylazetidin-2-one; or a mixture thereof.

In an embodiment, the cyclic amide solvent is N-methyl-2-pyrrolidone (NMP).

In an embodiment, the acid addition salts of vortioxetine are selected from hydrochloride, hydrobromide, hydrogen sulfate, phosphate, nitrate, acetate, ascorbate, benzoate, besylate, mesylate, succinate, oxalate, citrate, formate, fumarate, lactate, malonate, maleate, malate, palmitate, tartrate, and trifluoroacetate.

In a specific embodiment, the process for the preparation of vortioxetine (I) or its salt comprises the steps of:

(1) dissolving the compound (II) in an cyclic amide solvent;

(2) adding the compound (IIIa) or its salt to the reaction mixture of step (1);

(3) heating the reaction mixture of the above step (2) at temperature ranging between 80-180° C.;

(4) cooling the reaction mixture of the above step (3) at temperature of about 30° C.;

(5) isolating the product vortioxetine (I) or its salt.

The process of the present invention as per the specific embodiment described above is illustrated in the following Scheme-I,

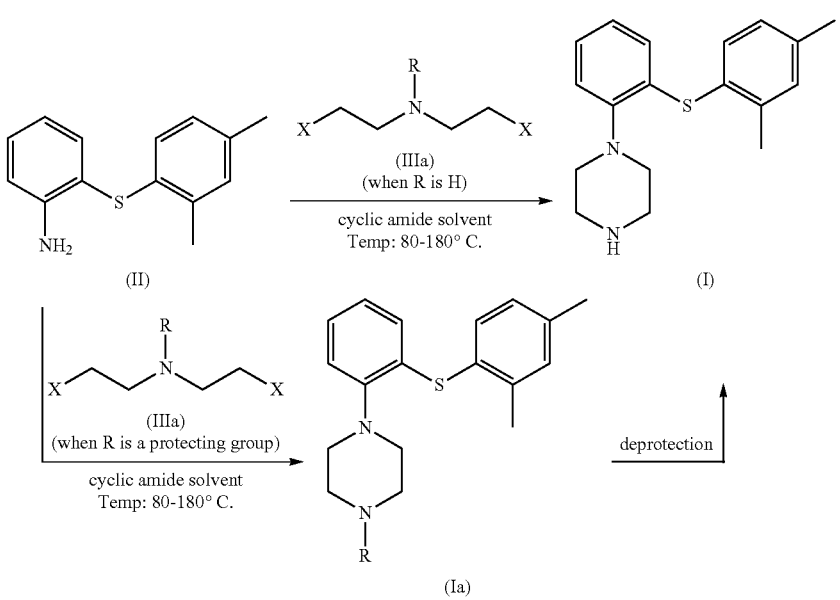

Scheme-I

In the compound bis(2-alkyl)amine (IIIa) of the above process (as depicted in the Scheme-I) wherein, 'X' is a leaving group selected from halogen such as Cl, Br, I or O-Mesyl (OMs), O-tosyl (OTs); and 'R' is H or a protecting group selected from carbonyl, acyl, sulfonyl, sulfenyl, silyl, benzyl, butyloxycarbonyl (Boc) or ethoxycarbonyl.

In an embodiment, the reaction is performed at a temperature ranging between 80-180° C., preferably 100-150° C.

The cyclic amide solvent used in the step-(1) of the above process (as depicted in the Scheme-I) is selected from the group consisting of N-methyl-2-pyrrolidone, caprolactam, 2-piperidinone, azetidin-2-one, N-methyl caprolactame, 1-methylpiperidin-2-one and 1-methylazetidin-2-one; or a mixture thereof.

In an embodiment, the amide solvent used in step-(1) of the above process (as depicted in the Scheme-I) is N-methyl-2-pyrrolidone (NMP).

The term 'temperature of about 30° C.' referred to in the step (4) of the above process (as depicted in the Scheme-I) can range from 25° C. to 35° C.

The term 'isolating the product' referred to in the step (5) corresponds to the steps involving separation of organic phase, filtration, evaporation of solvent, washing and drying; precipitation, filtration of precipitated product.

In an embodiment, the term 'deprotection' refers to the process step involving removal of N-protecting group. In general, the deprotection is achieved by the treatment of the N-protected compound with an acid or other deprotecting agent. For instance, when the protecting group is butyloxycarbonyl (Boc); the deprotection is achieved at the step involving formation of acid addition salt.

Similarly, the process of the present invention as per the specific embodiment described above is illustrated in the following Scheme-II, Scheme-II

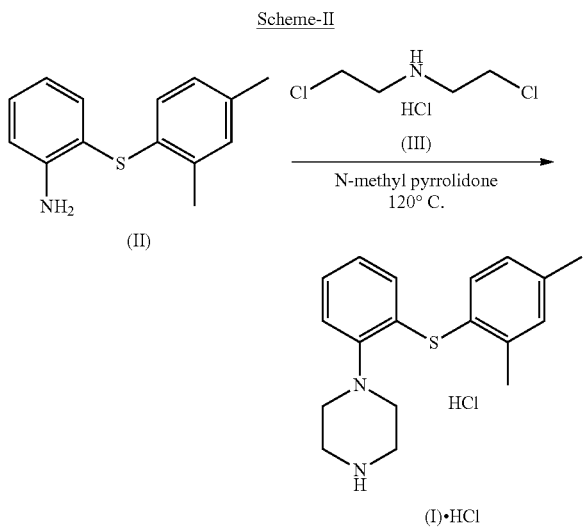

The process of the present invention as illustrated in the above Scheme-II comprises reaction of 2-((2,4-dimethylphenyl)thio)aniline the compound (II) with bis(2-chloroethyl)amine hydrochloride the compound (III) in a cyclic amide solvent such as N-methyl-2-pyrrolidone (NMP) at a temperature of 120-130° C., to provide vortioxetine hydrochloride with about 70% yield and a purity of at least 99% HPLC purity.

The term "about" in reference to the yield means a range of +5% of the specified yield.

It is evident from the processes reported in the prior art that the vortioxetine was obtained with low yield of about 53%; whereas the process of the present invention provided the pure vortioxetine in a yield of about 70% and purity of at least 99% (HPLC). It is further evident that the prior art process refers the use of various reagents and coupling agents such as acid binding agent, metal catalyst or a phosphine ligand; which are avoided in the currently presented improved process. This amounts to a significant advantage over the processes reported in the prior art.

Advantageously, the above identified elements of the process of the instant invention effectively contribute to the reduction of overall cost of the process.

In another aspect, there is provided Vortioxetine (I) hydrobromide having particle size distribution range of d (10) of about less than 12 μm, d (50) of about less than 40 μm or d (90) of about less than 180 μm; or any combination thereof.

In another aspect, there is provided Vortioxetine (I) hydrobromide having particle size distribution range of d (10) of between about 5 μm to about 12 μm.

In another aspect, there is provided Vortioxetine (I) hydrobromide having particle size distribution range of d (50) of between about 30 μm to about 40 μm.

In another aspect, there is provided Vortioxetine (I) hydrobromide having particle size distribution range of d (90) of between about 80 μm to about 180 μm.

The term "about" in reference to the particle size distribution range means a range of +5 μm of the specified d(10), d(50) or d(90) particle size.

The following Table-1 indicates the particle size range of Vortioxetine (I) hydrobromide as observed by the inventors:

TABLE 1

| Batch .No | D(10) μm | D(50) μm | D(90) μm |
|---|---|---|---|
| A | 10 | 36 | 100 |
| B | 9 | 33 | 109 |
| C | 11 | 35 | 176 |

The above particle size ranges were observed when measured by Malvern Mastersizer particle size analyzer equipped with a 30 mm lens Mastersizer 3000, hydroSM. In general, the particle size distribution may be achieved by the process of the present invention or alternatively by any one of the known methods reported in the art like milling, micronization, grinding or sieving, which may reduce the particle.

In another aspect, there is provided Vortioxetine (I) hydrobromide having particle size distribution range of d(10) between about 5 μm to about 12 μm, d(50) between about 30 μm to about 40 μm or d(90) between about 80 μm to about 180 μm; or any combination thereof.

In another aspect, there is provided a pharmaceutical composition comprising a therapeutically effective amount of Vortioxetine (I) hydrobromide having particle size distribution range of d (10) of about less than 12 μm, d (50) of about less than 40 μm or d (90) of about less than 180 μm; or any combination thereof.

In another aspect, there is provided a pharmaceutical composition comprising a therapeutically effective amount of Vortioxetine (I) hydrobromide having particle size distribution range of d(10) between about 5 μm to about 12 μm, d(50) between about 30 μm to about 40 μm or d(90) between about 80 μm to about 180 μm; or any combination thereof.

In another aspect, there is provided Vortioxetine (I) hydrobromide having specific surface area value from 0.05 to 2 m$^2$/g.

In another aspect, there is provided Vortioxetine (I) hydrobromide having specific surface area value from 0.1 to 1 m$^2$/g.

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present invention.

EXAMPLES

Example-1: Preparation of Vortioxetine Hydrochloride [the Compound (I).HCl]

Charged 30 mL of N-methyl-2-pyrrolidone (NMP) in a flask followed by the addition of 2-((2,4-dimethylphenyl)

thio)aniline (II) (10 g) and Bis(2-chloroethyl)amine hydrochloride (III) (15.6 g). The reaction mixture was heated at a temperature of 120-130° C. for 2 days. The reaction mixture was cooled to the temperature of 25-30° C., followed by the addition of water (100 mL). The obtained solid was filtered and dried under vacuum as Vortioxetine Hydrochloride [Yield 70%; Purity: 99.5% (HPLC)].

Example-2: Preparation of Vortioxetine Hydrobromide [the Compound (I).HBr]

Charged 50 mL of dichloromethane in a flask followed by the addition of Vortioxetine Hydrochloride (10 g) and 50 mL of 4% sodium hydroxide solution in water. The reaction mixture was stirred at a temperature of 25-30° C. and the separate organic layer was distilled out under vacuum. To the residue, was added 110 mL of isopropyl acetate and Hydrobromic acid (5.65 g) solution in water. The reaction mixture was stirred and filtered to provide Vortioxetine Hydrobromide [Yield 88%; Purity: 99.9% (HPLC)].

We claim:

1. A process for the preparation of vortioxetine (I) or a salt thereof of formula,

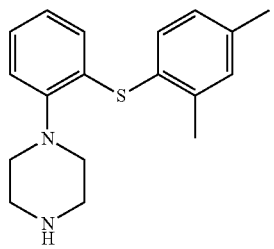

(I)

consisting of the steps of reacting 2-((2,4-dimethylphenyl)thio)aniline (II) of the following formula;

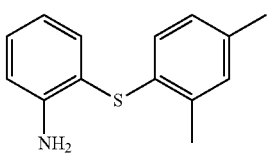

(II)

with bis(2-alkyl)amine (IIIa) or its salt of the following formula;

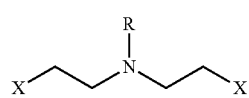

(IIIa)

wherein, X is a leaving group and R is H or a protecting group in a cyclic amide solvent, either providing compound (I) directly if R is H; or providing compound (Ia) if R is a protecting group,

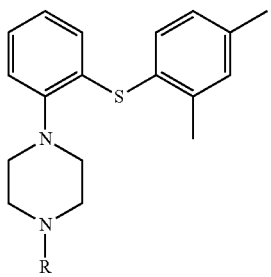

(Ia)

which on deprotection provides compound (I).

2. The process according to the claim 1, wherein the cyclic amide solvent is selected from the group consisting of N-methyl-2-pyrrolidone (NMP), caprolactam, 2-piperidinone, azetidin-2-one, N-methyl caprolactame, 1-methylpiperidin-2-one, 1-methylazetidin-2-one; and a mixture thereof.

3. The process according to the claim 1, wherein the reaction is performed at temperature ranging between 80-180° C.

4. The process according to the claim 1, wherein the product vortioxetine (I) or a salt thereof is obtained in a yield of about 70%.

5. The process according to the claim 1, wherein the product vortioxetine (I) or a salt thereof is obtained with in a purity of at least 99% (HPLC).

6. The process according to the claim 1, wherein the product vortioxetine (I) or a salt thereof is further transformed into another acid addition salt of vortioxetine.

7. A process for the preparation of vortioxetine (I) or a salt thereof of formula,

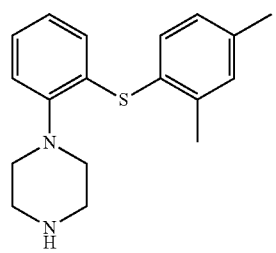

(I)

comprising the steps of, reacting 2-((2,4-dimethylphenyl)thio)aniline (II) of formula;

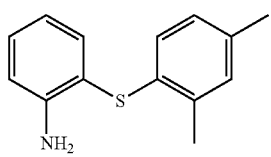

(II)

with bis(2-alkyl)amine hydrochloride (III) of formula;

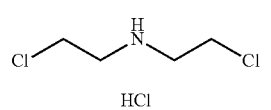

(III)

in N-methyl-2-pyrrolidone (NMP) solvent, at temperature ranging between 80-180° C.; and optionally transforming vortioxetine (I) or a salt thereof into its another acid addition salt.

8. A compound Vortioxetine (I) hydrobromide having particle size distribution range of d(10) between about 5 μm to about 12 μm, or d(50) between about 35 μm to about 40 μm or d(90) between about 80 μm to about 180 μm; or any combination thereof.

9. A compound Vortioxetine (I) hydrobromide having specific surface area value of at least 1 $m^2/g$ and not more than 2 $m^2/g$.

* * * * *